(12) United States Patent
Kapadia

(10) Patent No.: US 8,597,225 B2
(45) Date of Patent: Dec. 3, 2013

(54) METHOD FOR INCREASING BLOOD FLOW IN OR ABOUT A CARDIAC OR OTHER VASCULAR OR PROSTHETIC STRUCTURE TO PREVENT THROMBOSIS

(75) Inventor: Samir Kapadia, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 162 days.

(21) Appl. No.: 13/190,512

(22) Filed: Jul. 26, 2011

(65) Prior Publication Data

US 2012/0022427 A1 Jan. 26, 2012

Related U.S. Application Data

(60) Provisional application No. 61/367,472, filed on Jul. 26, 2010.

(51) Int. Cl.
*A61M 5/00* (2006.01)
*A61M 25/00* (2006.01)

(52) U.S. Cl.
USPC .............................. 604/9; 604/264; 604/275

(58) Field of Classification Search
USPC ............... 604/8–10, 20, 93.01, 95.01, 96.01, 604/102.01, 104, 118, 121, 124, 140, 146, 604/165.01–165.04, 174, 175, 177, 178, 604/181, 187, 239, 257, 275; 600/104, 116, 600/129, 153, 156, 158; 239/525, 532
See application file for complete search history.

(56) References Cited

U.S. PATENT DOCUMENTS

| 6,685,666 B1 | 2/2004 | Fontenot |
| 2005/0222533 A1 | 10/2005 | Chanduszko et al. |
| 2009/0149949 A1 | 6/2009 | Quinn |

*Primary Examiner* — Melanie Hand
(74) *Attorney, Agent, or Firm* — Tarolli, Sundheim, Covell & Tummino LLP

(57) ABSTRACT

A method is provided for increasing blood flow in or about a cardiac structure to prevent thrombosis. One step of the method includes providing an implantable sprayer having an elongated tubular body with proximal and distal end portions. The distal end portion includes at least one opening and an anchoring mechanism. The distal end portion of the implantable sprayer is inserted into a cardiac chamber that includes the cardiac structure. The anchoring mechanism is then deployed so that the distal end portion of the implantable sprayer is secured in or about the cardiac structure. Next, the proximal end portion is anastomosed with an artery so that blood flows through the elongated tubular body of the implantable sprayer and is sprayed out of the at least one opening to continuously circulate blood in or about the cardiac structure.

8 Claims, 16 Drawing Sheets

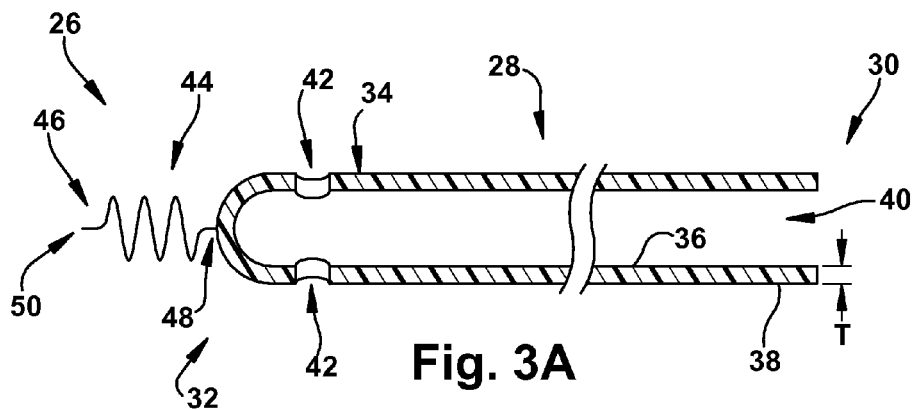
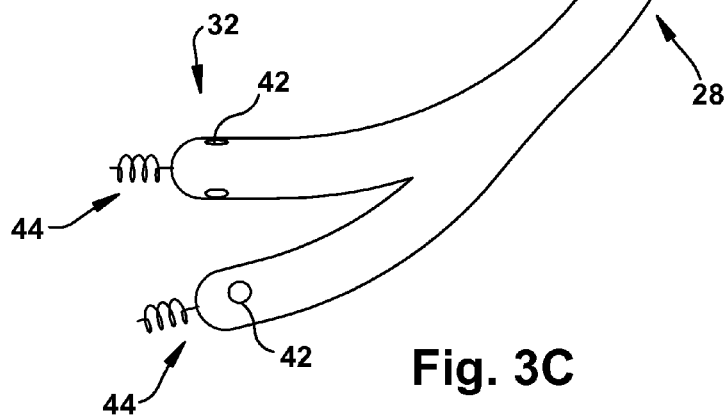

METHOD FOR INCREASING BLOOD FLOW IN OR ABOUT A CARDIAC OR OTHER VASCULAR OR PROSTHETIC STRUCTURE TO PREVENT THROMBOSIS

RELATED APPLICATION

This application claims priority from U.S. Provisional Patent Application Ser. No. 61/367,472, filed Jul. 26, 2010, the subject matter of which is hereby incorporated by reference in its entirety.

FIELD OF THE INVENTION

The present invention relates to apparatus and methods for increasing blood flow in or about a cardiac structure, and more particularly to apparatus and methods for increasing blood flow in or about a cardiac or other vascular or prosthetic structure to prevent thrombosis.

BACKGROUND OF THE INVENTION

Arrhythmias are abnormal heart rhythms that may cause the heart to function less effectively. Atrial fibrillation (AF) is the most common abnormal hear rhythm. Research has indicated that as many as ninety-percent of all thrombi formed during AF originate in the left atrial appendage (LAA). The LAA is a remnant of an original embryonic left atrium that develops during the third week of gestation. It is located high on the free wall of left atrium. Long, tubular, and hook-like in structure, the LAA is connected to the left atrium by a narrow junction, referred to as the ostium. The precise physiological function of the LAA remains uncertain.

The high rate of thrombus formation in the LAA is believed to be attributable to its physical characteristics. Blood easily stagnates and clots in the long, tubular body of the LAA or at its narrow ostium. In contrast, the right atrial appendage, which is a wide, triangular appendage connected to the right atrium by a broad ostium is infrequently the site of thrombus formation. Thrombus formation in the LAA is further promoted by the numerous tissue folds (i.e., crenellations) on its interior surface. These crenellations are particularly hospitable to blood stagnation and clotting, especially when the heart is not functioning at maximum capacity. Thrombi formed in the LAA can re-enter the circulation upon conversion of AF to normal rhythm (i.e., cardioversion).

Obliteration and occlusion are controversial because of the uncertain physiological role of the LAA. Reports have suggested that obliteration of the LAA may decrease atrial compliance and diminish peptide hormone atrial natriuretic factor secretion. Furthermore, while properly positioned filter devices prevent migration of thrombi into the circulatory system, such devices cannot inhibit thrombus formation within the LAA. Consequently, in the event a filter device is dislodged or ineffectively sealed against the LAA ostium, clots held at the LAA ostium by the filter can be released into the circulation.

SUMMARY OF THE INVENTION

In accordance with one aspect of the present invention, a method is provided for increasing blood flow in or about a cardiac structure to prevent thrombosis. One step of the method includes providing an implantable sprayer comprising an elongated tubular body having proximal and distal end portions. The distal end portion includes at least one opening and an anchoring mechanism. The distal end portion of the implantable sprayer is inserted into a cardiac chamber that includes the cardiac structure. The anchoring mechanism is then deployed so that the distal end portion of the implantable sprayer is secured in or about the cardiac structure. Next, the proximal end portion is anastomosed with an artery so that blood flows through the elongated tubular body of the implantable sprayer and is sprayed out of the at least one opening to continuously circulate blood in or about the cardiac structure.

In accordance with another aspect of the present invention, a method is provided for increasing blood flow in a left atrial appendage (LAA) to prevent thrombosis. One step of the method includes providing an implantable sprayer comprising an elongated tubular body having proximal and distal end portions. The distal end portion includes at least one opening and an anchoring mechanism. The distal end portion of the implantable sprayer is inserted into a cardiac chamber that includes the cardiac structure. The anchoring mechanism is deployed so that the distal end portion of the implantable sprayer is secured in the LAA. The proximal end portion is then anastomosed with a subclavian artery so that blood flows through the elongated tubular body of the implantable sprayer and is sprayed out of the at least one opening to continuously circulate blood in the LAA.

In accordance with another aspect of the present invention, a method is provided for promoting circulation within a LAA. One step of the method includes providing an implantable sprayer. The implantable sprayer comprises an elongated tubular body having proximal and distal end portions. The distal end portion includes at least one opening and an anchoring mechanism. Next, the distal end portion of the implantable sprayer is inserted into a left atrium that includes the LAA. The anchoring mechanism is then deployed so that the distal end portion of the implantable sprayer is secured in the left atrial appendage. The proximal end portion is anastomosed with a portion of an interatrial septum so that blood is withdrawn from the LAA through the at least one opening and into a right atrium to prevent or mitigate blood stasis in the LAA.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 3A is a side cross-sectional view showing the distal end portion of the implantable sprayer in FIG. 2;

FIG. 3B is a cross-sectional view taken along Line 3B-3B in FIG. 2;

FIG. 3C is a perspective view showing an alternative configuration of the implantable sprayer in FIG. 2;

DETAILED DESCRIPTION

Figure 1:
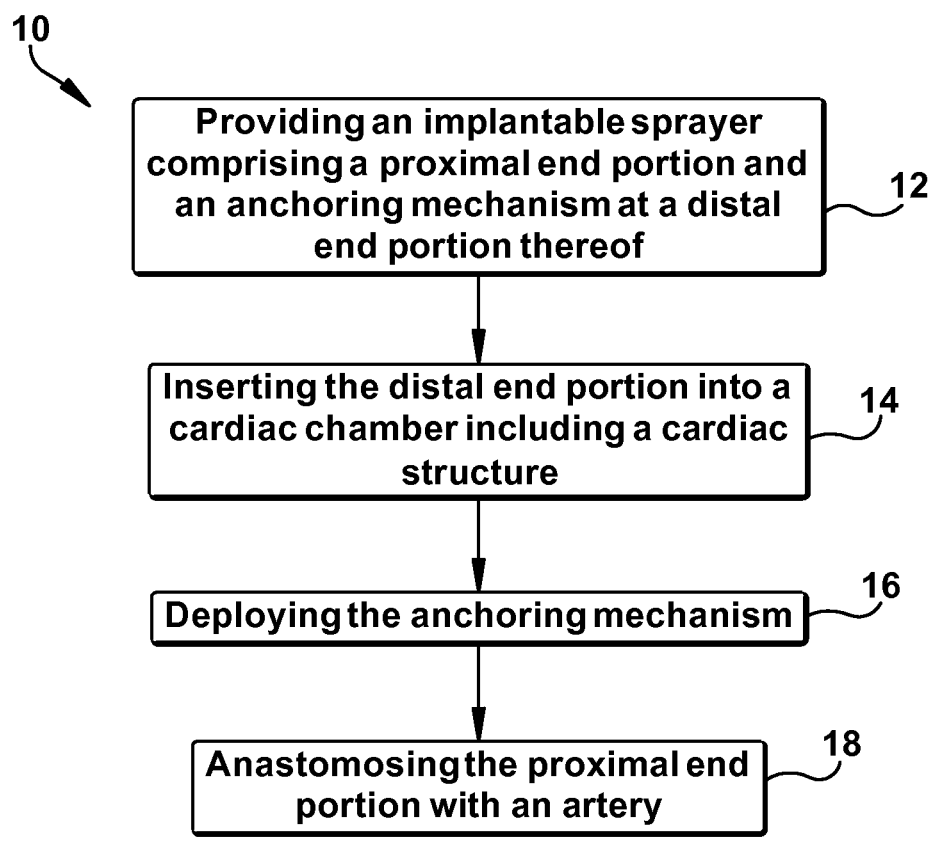
FIG. 1 is a process flow diagram illustrating a method for increasing blood flow in or about a cardiac structure to prevent thrombosis according to one aspect of the present invention.

The present invention relates to apparatus and methods for increasing blood flow in or about a cardiac structure, and more particularly to a method 10 (FIG. 1) and apparatus (FIG. 2) for increasing blood flow in or about a cardiac structure 20 (FIG. 5) or other vascular or prosthetic structure to prevent thrombosis. Certain cardiac structures 20, such as the left atrial appendage 22 (LAA) and implanted prosthetic cardiac valves 24 can lead to thrombus formation as a result of blood stasis on or about the cardiac structures. Current techniques for preventing or mitigating thrombus formation include surgical obliteration of and/or blood flow restriction to such cardiac structures 20. Unlike these techniques, however, the method 10 of the present invention does not restrict blood flow in or about cardiac structures 20. Rather, the present invention enhances or increases blood flow in or about cardiac structures 20. Advantageously, the method 10 of the present invention promotes blood circulation in and around a cardiac structure 20 so that blood continually flushes at least a portion of the cardiac structure and thereby mitigates or prevents thrombus formation.

Referring to FIG. 1, one aspect of the present invention includes a method 10 for increasing blood flow in or about a cardiac structure 20 to prevent thrombosis in a subject. As used herein, the term "subject" can refer to any animal, including, but not limited to, humans and non-human animals (e.g., rodents, arthropods, insects, fish), non-human primates, ovines, bovines, ruminants, lagomorphs, porcines, caprines, equines, canines, felines, ayes, etc.). Cardiac structures 20 in or around which blood flow can be increased include both native and non-native anatomical structures. Examples of native anatomical structures can include the LAA 22, a right atrial appendage (not shown), or any other structure (e.g., vascular) that is formed from a tissue, bone, or ligament of a subject.

Examples of non-native anatomical structures can include implantable prosthetic medical devices, such as cardiac valves (e.g., mechanical or bioprosthetic valves), annuloplasty rings (not shown), ventricular assist devices (not shown), and the like, that are capable of promoting or causing thrombus formation.

At Step 12 of the method 10, an implantable sprayer 26 (FIG. 2) is provided. The implantable sprayer 26 has an elongated, tubular body 28 with oppositely disposed proximal and distal end portions 30 and 32. The elongated tubular body 28 includes at least one side wall 34 (FIGS. 3A-B) having a thickness T defined by an inner surface 36 and an outer surface 38. As shown in FIGS. 3A-B, a lumen 40 defined by the inner surface 36 extends between the proximal and distal end portions 30 and 32. Although a single lumen 40 is shown in FIGS. 3A-B, it will be appreciated that the implantable sprayer 26 can include more than one lumen (e.g., a double lumen). Depending upon the particular application for which the implantable sprayer 26 is intended, the diameter of the lumen 40 can be varied as needed. Also depending upon the particular application, the implantable sprayer 26 can have any appropriate length and side wall thickness T (e.g., a thin, double-walled configuration).

The implantable sprayer 26 can have a flexible or semirigid configuration and be made of any one or combination of biocompatible materials, such as medical grade silicon or plastic (e.g., rubber, urethanes, polyethylene, polypropylene, ABS, PVC, Nylon, latex, etc.) to impart the implantable sprayer with a desired elasticity and flexibility. For example, all or only a portion of the side wall 34 can be reinforced to prevent or mitigate kinking, increase bend radius, and/or accommodate high pressure flow rates. All or only a portion of the implantable sprayer 26 can be treated (e.g., coated) with an anti-coagulant (e.g., heparin) and/or anti-platelet agent. Additionally, all or only a portion of the implantable sprayer 26 can be treated to be radiopaque.

Figure 2:
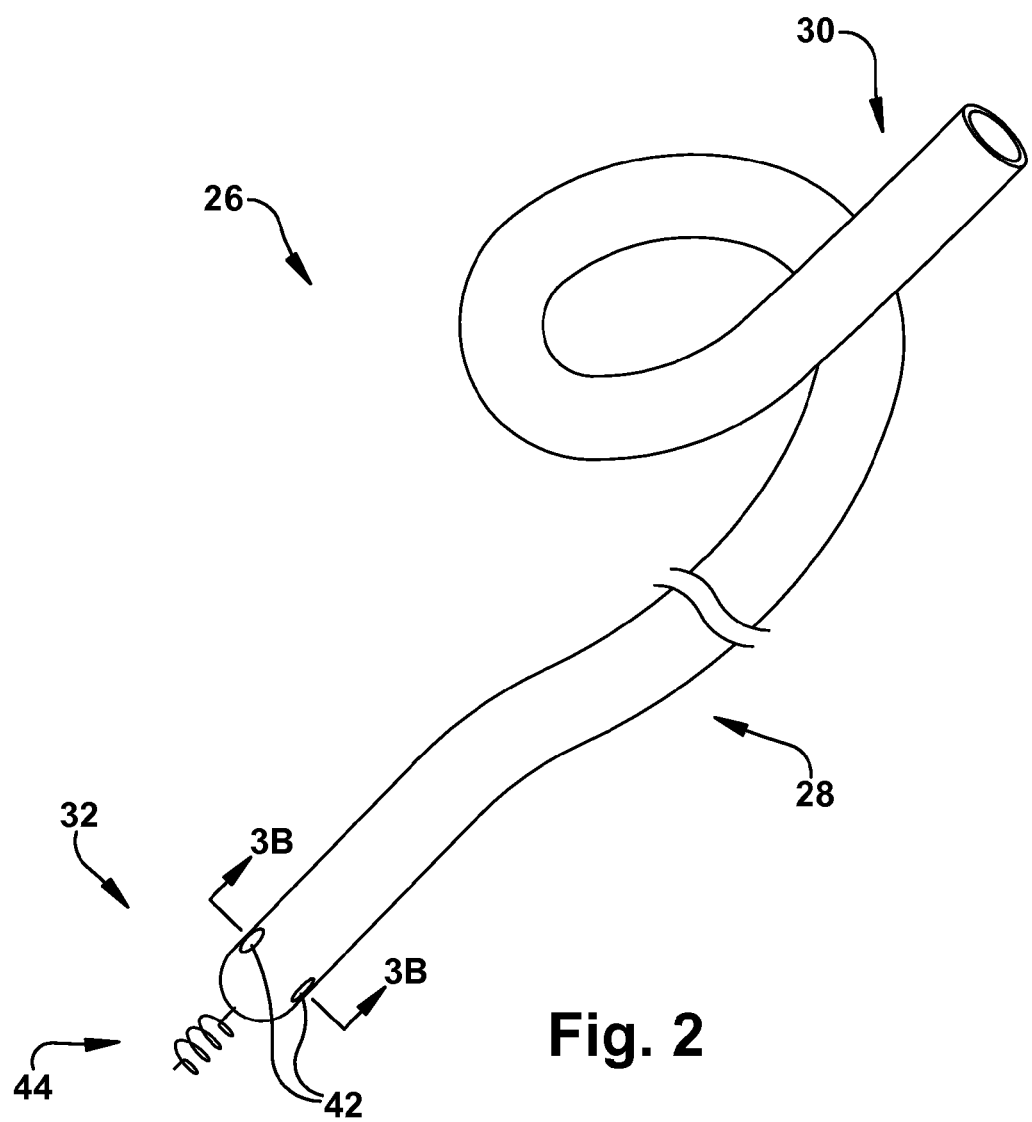
FIG. 2 is a perspective view showing an implantable sprayer comprising a distal end portion, a proximal end portion, and an anchoring mechanism constructed in accordance with another aspect of the present invention.

As shown in FIG. 2, the distal end portion 32 of the implantable sprayer 26 has a generally conical or bullet-shaped configuration and includes at least one opening 42. The at least one opening 42 is configured to facilitate blood flow from the lumen 40 of the elongated tubular body 28 out of the distal end portion 32. The at least one opening 42 (FIGS. 3A-B) extends between the inner and outer surfaces 36 and 38 of the side wall 34. Although only two openings 42 are shown in FIG. 2 and FIGS. 3A-B, it will be appreciated that the distal end portion 32 can include any desired number of openings having a size and shape that facilitates blood flow therethrough. Additionally, it will be appreciated that alternative configurations of the distal end portion 32 are possible, such as the Y-shaped configuration shown in FIG. 3C.

The distal end portion 32 of the implantable sprayer 26 also includes an anchoring mechanism 44 for securing the distal end portion in or about a cardiac structure 20. The anchoring mechanism 44 can have any configuration that enables the distal end portion 32 to be securely positioned in or about a cardiac structure 20 and thereby ensure that blood can be continuously circulated in or about the cardiac structure. As shown in FIG. 2 and FIGS. 3A-B, one example of the anchoring mechanism 44 includes a spiral-shaped member 46 having first and second ends 48 and 50. The first end 48 of the spiral-shaped member 46 is securely attached to a portion of the side wall 34 comprising the distal end portion 32 of the implantable sprayer 26. The second end 50 of the spiral-shaped member 46 includes a sharpened point to facilitate entry of the spiral-shaped member into cardiac tissue. Although only one spiral-shaped member 46 is shown in FIG. 2 and FIGS. 3A-B, it will be appreciated that the anchor mechanism 44 can comprise any number of spiral-shaped members.

Figure 4A:
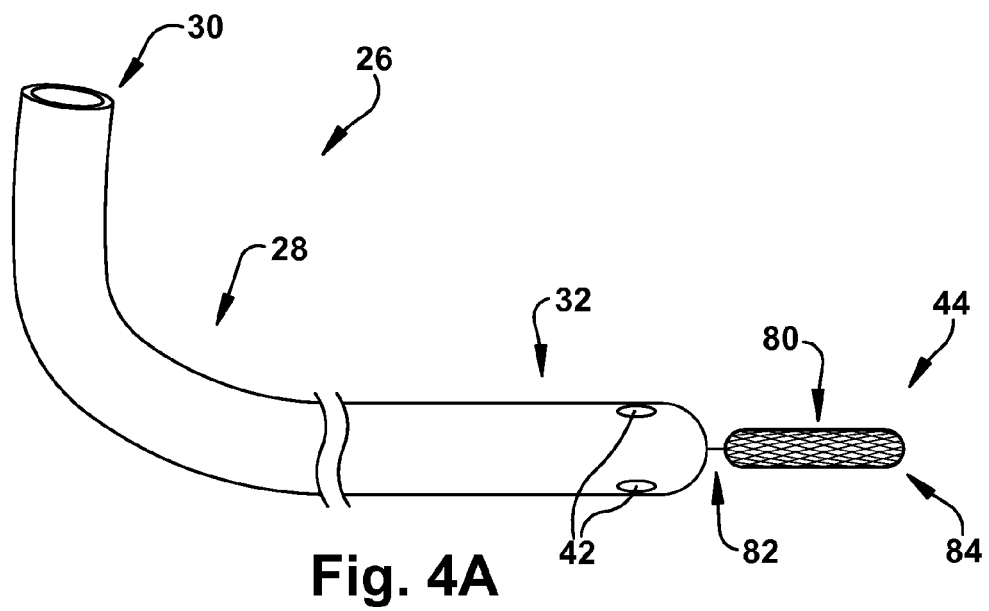
FIG. 4A is a perspective view showing an alternative configuration of the anchoring mechanism in FIG. 2 comprising an expandable support member (collapsed configuration)
Figure 4B:
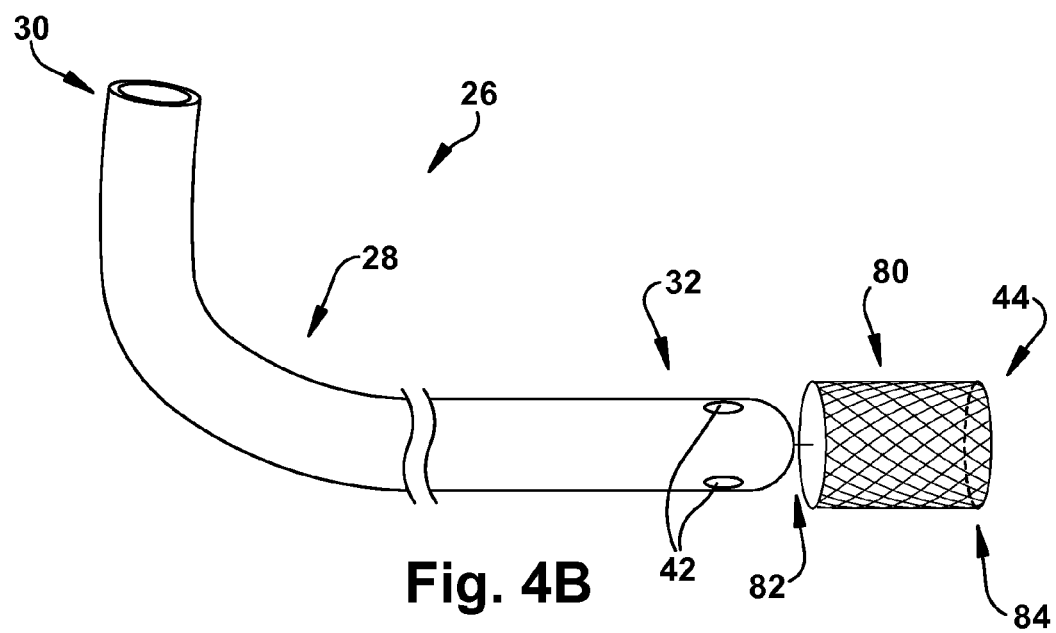
FIG. 4B is a perspective view showing the expandable support member in FIG. 4A having an expanded configuration.

Other configurations of the anchoring mechanism 44 are illustrated in FIGS. 4A-D. As shown in FIGS. 4A-B, for example, the anchoring mechanism 44 can comprise an expandable support member 80 having oppositely disposed first and second ends 82 and 84. The first end 82 of the expandable support member 80 can be securely connected to the distal end portion 32 of the implantable sprayer 26. The structure of the expandable support member 80 may be a mesh, a zigzag wire, a spiral wire, an expandable stent, or other similar configuration that allows the expandable support member to be collapsed (FIG. 4A) and expanded (FIG. 4B). The expandable support member 80 can be self-expanding or selectively expandable using, for example, tactile force or an expansion mechanism (not shown).

The expandable support member 80 can be comprised of an elastic material, such as cobalt-nickel alloys (e.g., Elgiloy), titanium, nickel-titanium alloys (e.g., Nitinol), cobalt-chromium alloys (e.g., Stellite), nickel-cobalt-chromium-molybdenum alloys (e.g., MP35N), graphite, ceramic, stainless steel, and plastics. The expandable support member 80 may also be made of a radio-opaque material or include radio-opaque markers to facilitate fluoroscopic visualization.

The flexible and expandable properties of the expandable support member 80 can facilitate percutaneous delivery of the implantable sprayer 26, while also allowing the expandable support member to conform to a portion of a cardiac structure 20, such as the LAA 22. As shown in the expanded configuration of FIG. 4B, the expandable support member 80 has a circular cross-sectional shape; however, it will be appreciated that the expandable support member can have any cross-sectional shape to conform to the shape of a cardiac structure 20. By conforming to at least a portion of the interior surface of a LAA 22, for example, the expanded configuration of the expandable support member 80 can secure the distal end portion 32 of the implantable sprayer 26 within the LAA while also promoting blood circulation therein.

Figure 4C:
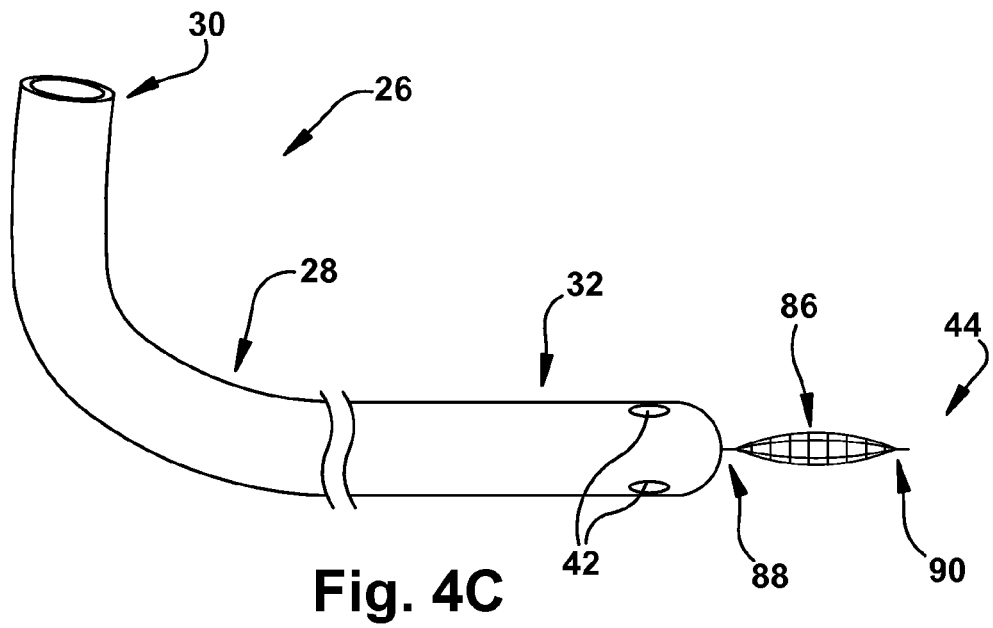
FIG. 4C is a perspective view showing an alternative configuration of the anchoring mechanism in FIG. 2 comprising a septal occluder (collapsed configuration)
Figure 4D:
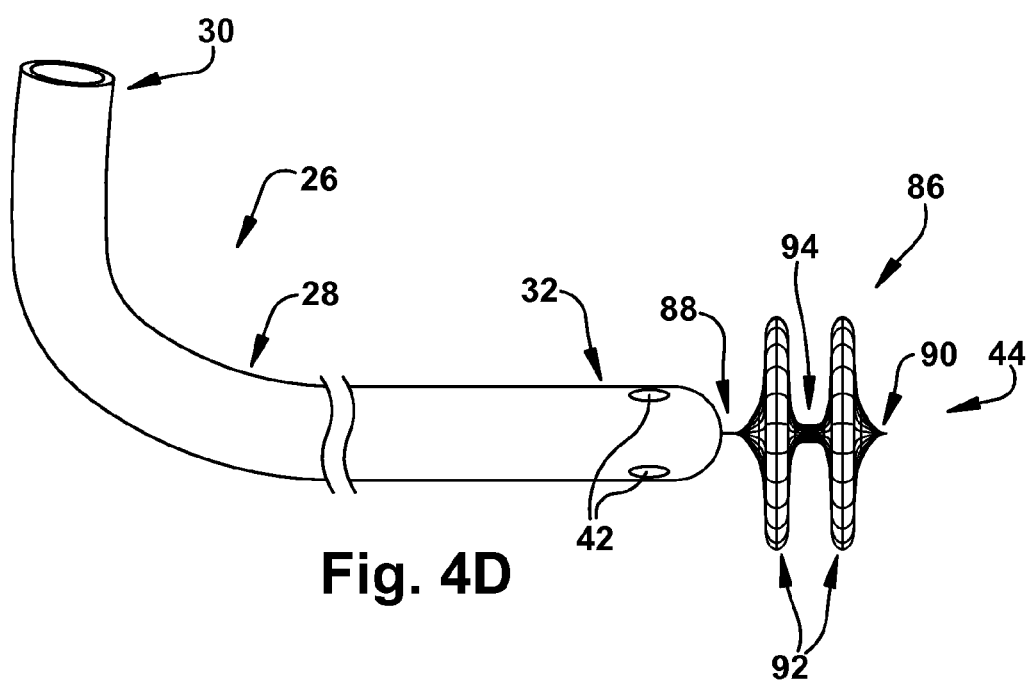
FIG. 4D is a perspective view showing the septal occluder in FIG. 4C having an expanded configuration.
Figure 5:
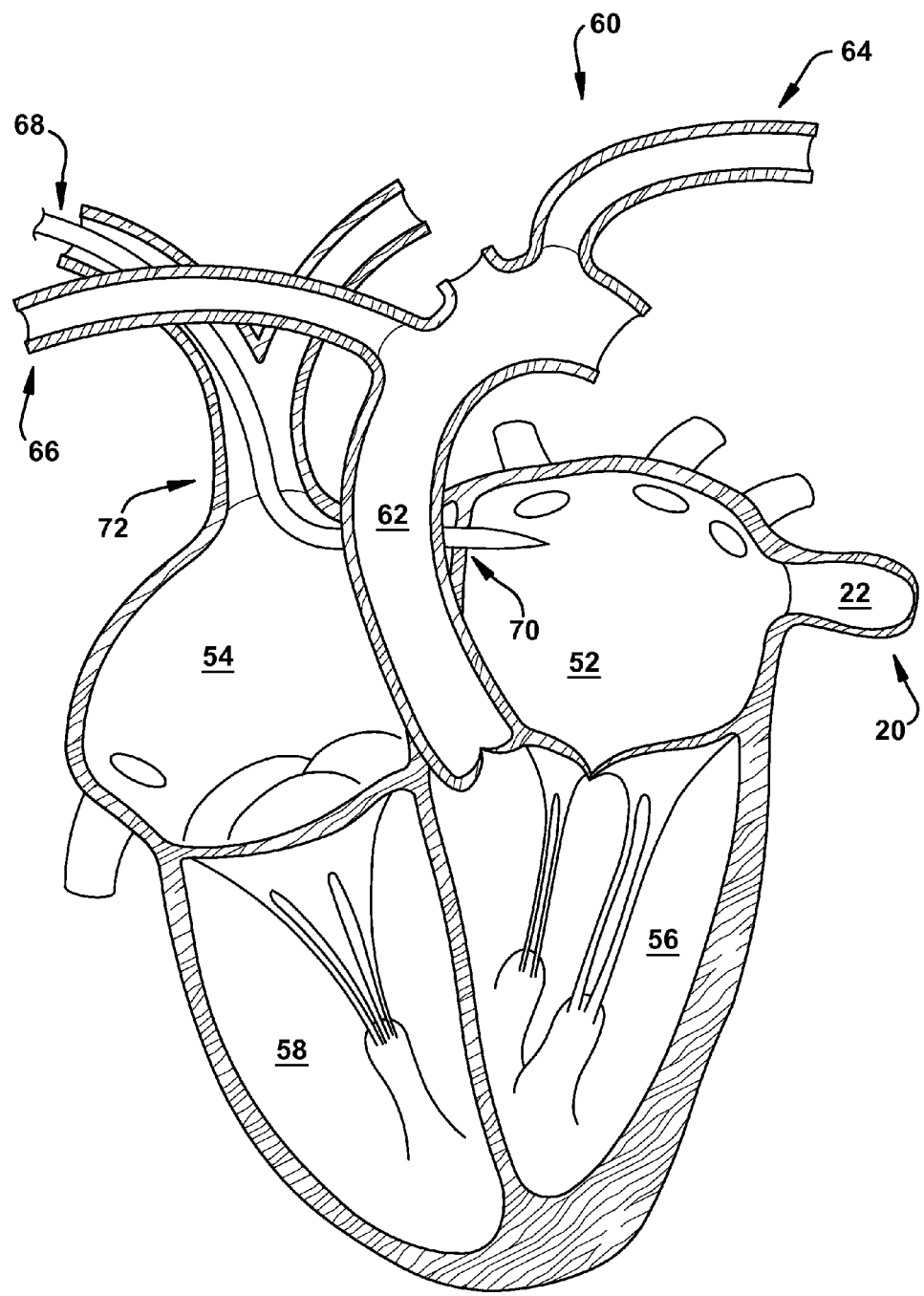
FIG. 5 is a cross-sectional view of a human heart showing a percutaneous tool being used to puncture the interatrial septum.

An alternative configuration of the anchoring mechanism 44 comprising a septal occluder 86 is illustrated in FIGS. 4C-D. The septal occluder 86 can include oppositely disposed first and second ends 88 and 90. The first end 88 can be securely connected to the distal end portion 32 of the implantable sprayer 26. Various types of septal occluders 86 are known in the art. For instance, the AMPLATZER® septal occluder, available from AGA Medical Corporation, located in Golden Valley, Minn., is a self-expandable, double disc device made from Nitinol wire mesh. The two discs are linked together by a short connecting waist corresponding to the size of the interatrial septum 70 (FIG. 5). To increase the closing ability of the AMPLATZER® septal occluder, the discs and the waist are filled with polyester fabric.

The septal occluder 86 (FIGS. 4C-D) may be configured in a manner similar to the AMPLATZER® septal occluder. For example, the septal occluder 86 can generally comprise any flexible frame structure that can passively anchor the distal end portion 32. The septal occluder 86 may be self-expandable and may be comprised of a flexible material, such as Nitinol. Alternatively, the septal occluder 86 may be selectively expandable using, for example, tactile force or an expansion mechanism (not shown). The septal occluder 86 can move between a collapsed configuration (FIG. 4C) and an expanded configuration (FIG. 4D). In the expanded configuration, the septal occluder 86 can include a plurality of oppositely opposed flexible discs 92, each of which are fluidly connected by a connecting waist 94 intermediate the flexible discs. The flexible discs 92 and the connecting waist 94 may be appropriately-sized so that the septal occluder 86, in its expanded configuration, can secure the distal end portion 32 of the implantable sprayer 26 in a LAA 22, for example, while also promoting blood circulation therein.

It will be appreciated that the anchoring mechanism 44 can have a variety of configurations other than those described above to facilitate anchoring of the distal end portion 32. For example, the anchoring mechanism 44 can comprise a manually-operated, clip-like structure (not shown) that can be selectively controlled to engage a cardiac structure 20 or tissue(s) surrounding the cardiac structure. Alternatively, the anchoring mechanism 44 can comprise a magnetic member (not shown) that can be magnetically attached to a metal-containing cardiac structure (e.g., a mechanical cardiac valve). Additionally, the anchoring mechanism 44 can optionally include a plurality of radially expandable tines (not shown) that can engage a cardiac structure 20 or tissue(s) surrounding the cardiac structure. The anchoring mechanism 44 can be deployed by tactile force, by an actuating mechanism (not shown) coupled to a sensor (e.g., a pressure sensor) (not shown), or by a remotely-controlled electrical system (e.g., an RF system) (not shown).

At Step 14, the implantable sprayer 26 is introduced into the subject using a known surgical technique so that the distal end portion 32 is positioned in or about a cardiac chamber that includes the cardiac structure 20. Examples of cardiac chambers can include the left and right atria 52 and 54 and the left and right ventricles 56 and 58. Although insertion of the implantable sprayer 26 into a subject is described herein using endoluminal and transapical approaches, it will be appreciated that other techniques can also be used, such as open heart surgery, thoracotomy, thoracoscopic, robotic implantation, left atrial dome insertion, and other minimally invasive techniques known in the art. It will also be appreciated that prior to introduction of the implantable sprayer 26 into the subject, the dimensions of the cardiac chamber(s) and/or the cardiac structure(s) 20 can be determined using one or a combination of known imaging techniques, such as magnetic resonance imaging (MRI), fluoroscopy, echocardiography (e.g., TEE or TTE imaging), computed tomography (CT), angiography, and ultrasound.

After the distal end portion 32 of the implantable sprayer 26 is advanced to the cardiac structure 20, the anchoring mechanism 44 is deployed so that the distal end portion is securely fixed or attached in or about the cardiac structure 20 (Step 16). The anchoring mechanism 44 is deployed to optimize the position of the distal end portion 32 and thereby ensure that blood can flow through the at least one opening 42 to continuously circulate blood in or about the cardiac structure 20. Depending upon the configuration of the anchoring mechanism 44, the anchoring mechanism is secured on or about the cardiac structure 20. Where the cardiac structure 20 is a native anatomical structure (e.g., cardiac tissue), the anchoring mechanism 44 can be directly attached to, or attached immediately adjacent, the cardiac structure. Alternatively, where the cardiac structure 20 is a non-native anatomical structure (e.g., an implanted prosthetic cardiac valve 24), the anchoring mechanism 44 can be attached directly to the cardiac structure to cardiac tissue adjacent the non-native anatomical structure.

At Step 18, the proximal end portion 30 of the implantable sprayer 26 is anastomosed with a portion of an artery 60. The proximal end portion 30 can be anastomosed with any artery 60, depending upon the location of the implantable sprayer 26 and the desired rate of blood flow through the implantable sprayer. Examples of arteries 60 that can be anastomosed with the proximal end portion 30 include the aorta 62 (e.g., the ascending aorta, the aortic arch, and the descending aorta), the left subclavian artery 64, the right subclavian artery 66, the left common carotid artery (not shown), the right common carotid artery (not shown), the brachiocephalic artery (not shown), and the femoral artery (not shown). The proximal end portion 30 can be introduced to the artery 60 for anastomosis using a variety of approaches and techniques. For example, a sheath (not shown) can be introduced in the artery 60. The proximal end portion 30 can then be introduced into the catheter, after which the implantable sprayer 26 can be secured to the sheath.

Anastomosis of the proximal end portion 30 with an artery 60—as opposed to a vein (not shown)—is advantageous for several reasons. First, blood flowing through arteries 60 is oxygenated (with the exception of the pulmonary artery), whereas blood flowing through veins is deoxygenated (with the exception of the pulmonary veins). It would be undesirable to continuously circulate deoxygenated blood in a cardiac chamber (i.e., the left atrium 52 or left ventricle 56) that requires high oxygen content to properly function. Second, arteries 60 are comprised of a thick, elastic muscle layer, whereas veins are comprised of a thin, elastic layer. Anastomosis of an implantable medical device (e.g., the implantable sprayer 26) with a vein would not be desirable as the the thin, elastic composition of the vein may easily tear or rupture. Finally, the fact that arterial blood pressure is significantly higher than venous blood pressure counsels against anastomosis of an implantable medical device (e.g., the implantable sprayer 26) with a vein for applications where increased blood flow through the implantable medical device is optimal.

Anastomosis of the proximal end portion 30 with a portion of the artery 60 causes blood to flow through the elongated tubular body 28 and be sprayed out of the at least one opening 42. Blood flow through the at least one opening 42 continuously circulates blood in or around the cardiac structure 20 in a pulsatile manner. Advantageously, the continuous flow of blood in or about the cardiac structure 20 prevents or mitigates blood stagnation and thus prevents or mitigates thrombus formation. Consequently, the method 10 of the present invention can effectively be used to treat conditions associated with thrombus formation, such as stroke, transient ischemic attacks, heart attack, and pulmonary embolism.

FIGS. 5-9 illustrate one example of the present invention comprising a percutaneous or endoluminal method for increasing blood flow in the LAA 22 to prevent thrombosis. One step of the method can include selecting an implantable sprayer 26, such as the one shown in FIGS. 2-3B and described above. The implantable sprayer 26 can be configured for implantation into the subject based on one or more imaging and/or flow analysis studies (e.g., MRI, fluoroscopy, echocardiography, CT, angiography, etc.).

Once an appropriately-sized implantable sprayer 26 has been selected, a vein (e.g., a femoral vein) of the subject can be accessed using, for example, a hypodermic needle (not shown). A percutaneous tool 68 (FIG. 5) can then be used to puncture the interatrial septum 70 using a known transseptal approach. During such an approach, a physician may use a transseptal introducer (not shown) and a long, curved needle (not shown) for left atrial access from the venous system. The introducer, which may be curved to facilitate access to a desired portion of the left-heart anatomy, can include a sheath (not shown) and a separate dilator (not shown). The curved needle may be, for example, a stainless steel Brockenbrough curved needle or a trocar.

The curved needle can then be used to make a transseptal puncture after the curved transseptal introducer is used to guide the needle into position. In particular, once the transseptal introducer is in the right atrium 54, a distal tip of the guiding introducer can be positioned against a puncture site, such as the fossa ovalis (not shown in detail) in the inter-atrial septal wall 70. Next, a Brockenbrough needle can be advanced distally through the transseptal introducer beyond the distal end of the introducer until it punctures the fossa ovalis. If the introducer includes a dilator, the dilator may be advanced with a needle through the punctured fossa ovalis to prepare an access port through the septum 70 into the left atrium 52. Once the sheath has been seated across the septum 70 and in the left atrium 52, the dilator, if present, and the needle may be withdrawn from the sheath. This sheath can then provide luminal access into the left atrium 52.

Figure 6:
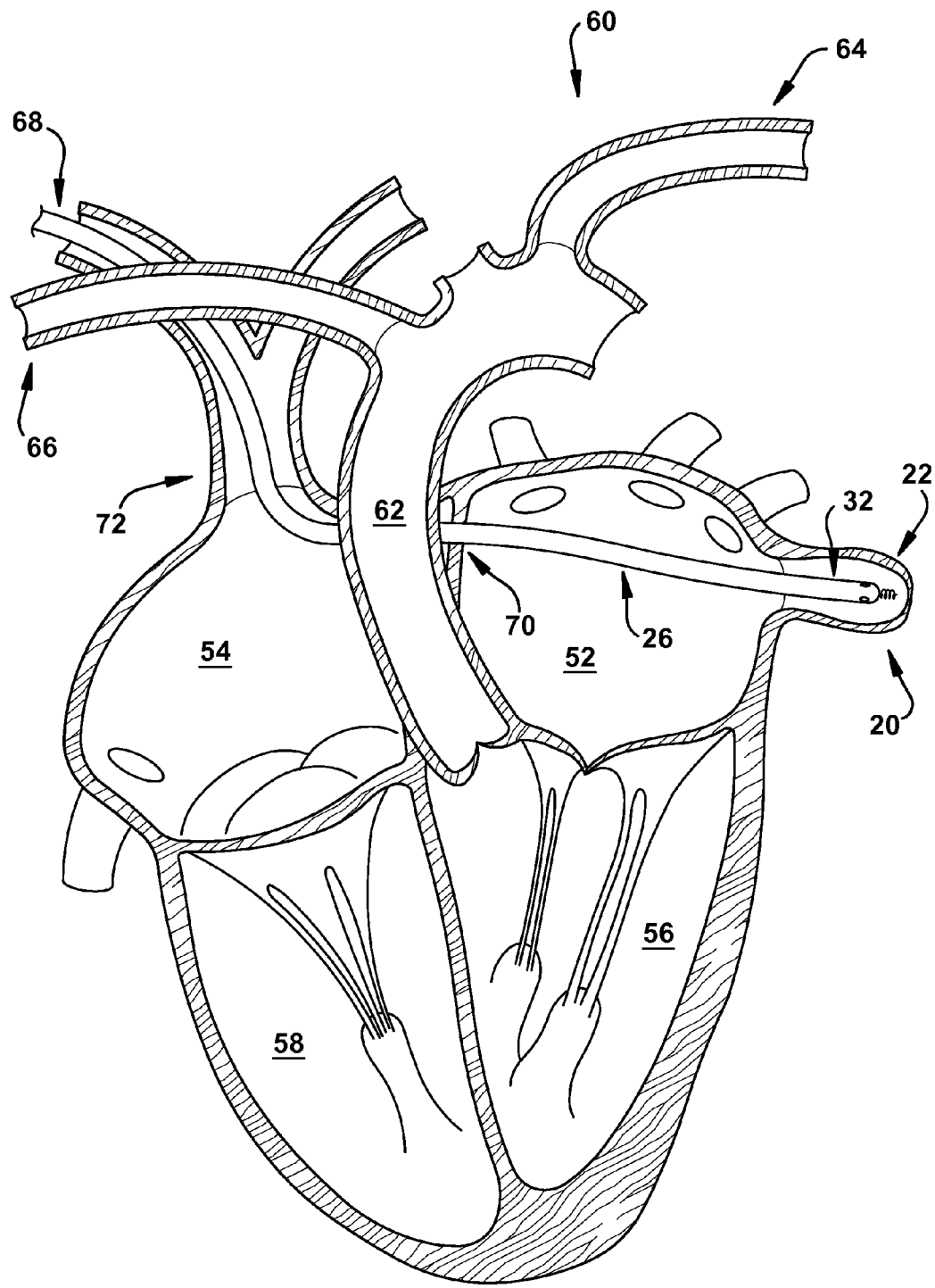
FIG. 6 is a cross-sectional view of the human heart in FIG. 5 showing the distal end portion of the implantable sprayer (FIG. 2) being inserted through a transseptal puncture and advanced into a left atrial appendage (LAA)

After forming the transseptal puncture, the implantable sprayer 26 can be loaded into the sheath and advanced through the venous vasculature. As shown in FIG. 6, the distal end portion 32 of the implantable sprayer 26 can be advanced through the superior vena cava 72, into the right atrium 54, and through the transseptal puncture into the left atrium 52. The distal end portion 32 can then be further advanced to a desired position within the LAA 22.

Figure 7:
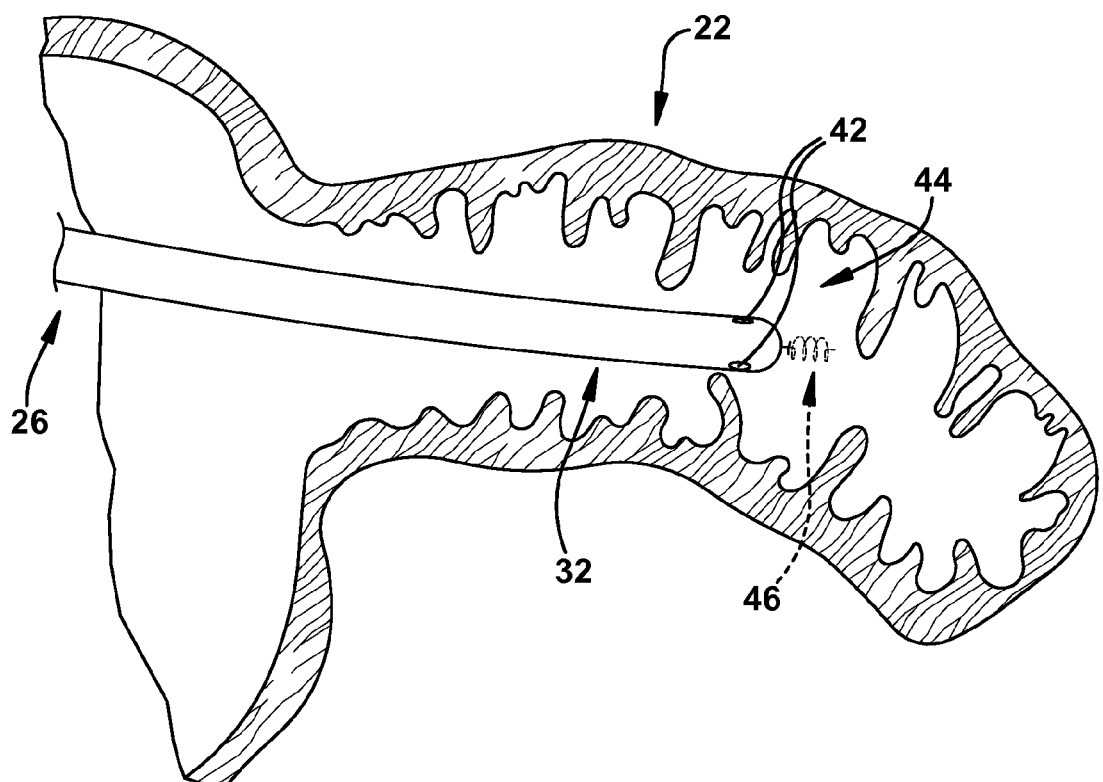
FIG. 7 is a magnified cross-sectional view of the LAA in FIG. 6 showing the anchoring mechanism of the implantable sprayer is secured in the LAA.

Once the distal end portion 32 is appropriately positioned within the LAA 22, the anchoring mechanism 44 (e.g., the spiral-shaped member 46) can be deployed to securely anchor the distal end portion. For example, an axial force can be applied to the implantable sprayer 26 (e.g., by tactile means) so that the second sharpened end 50 of the spiral-shaped member 46 pierces a portion of the tissue comprising the LAA 22. Next, a sufficient amount of torque can be applied to the implantable sprayer 26 to cause the spiral-shaped member 46 to become securely embedded with the tissue of the LAA 22 (FIG. 7).

Figure 8:
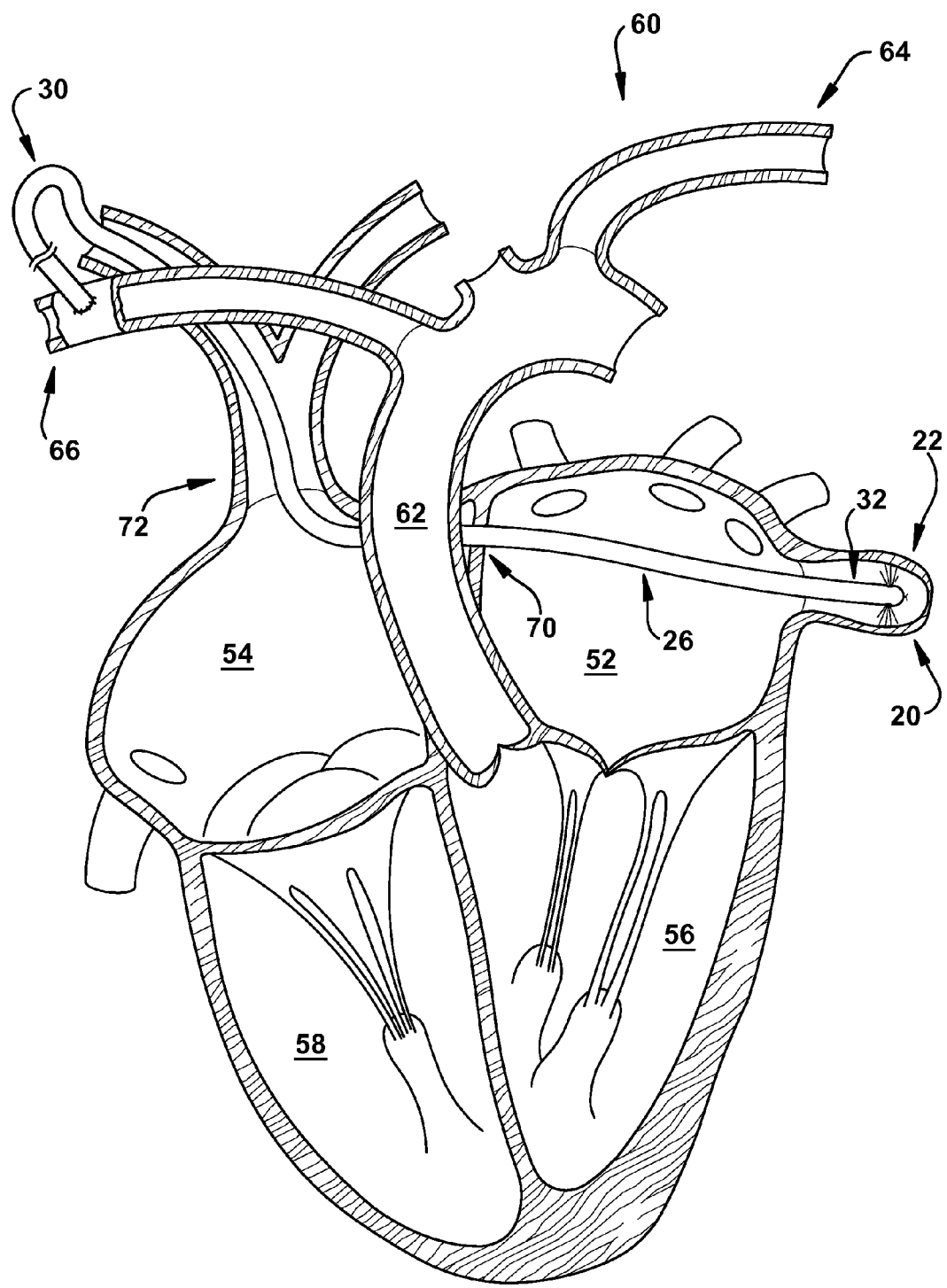
FIG. 8 is a cross-sectional view of the human heart in FIG. 6 showing the proximal end portion of the implantable sprayer anastomosed with a right subclavian artery.
Figure 9:
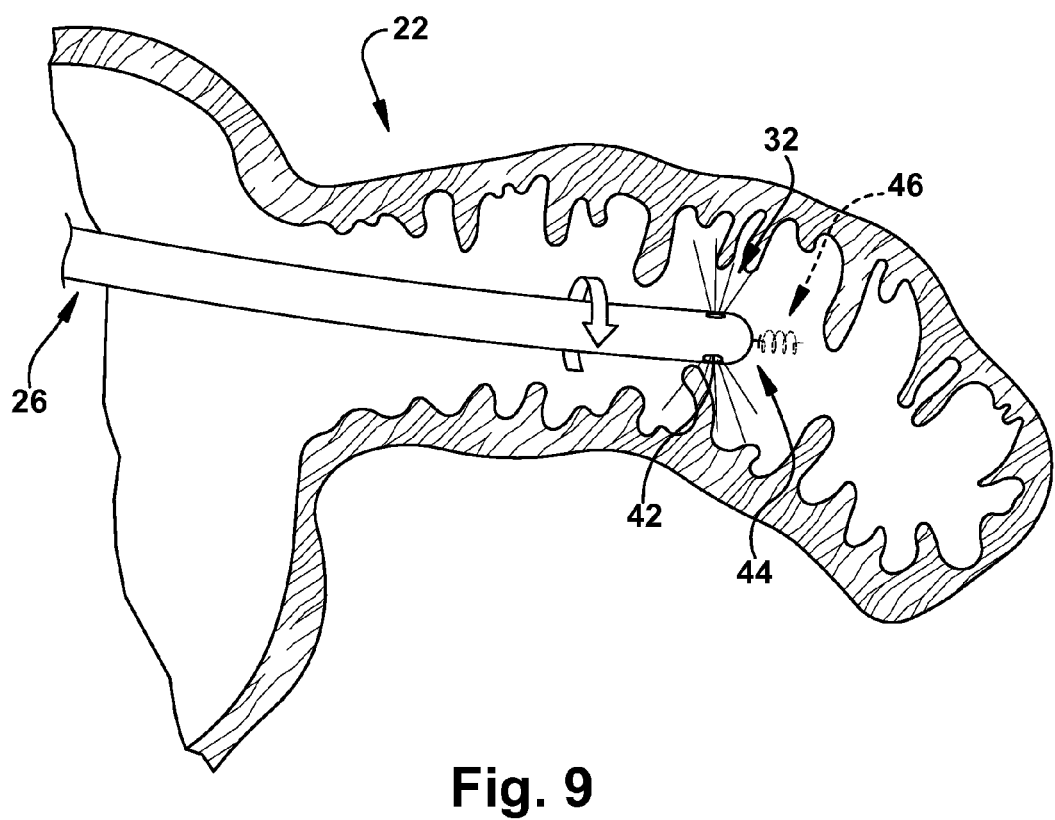
FIG. 9 is a magnified cross-sectional view of the LAA in FIG. 8 showing blood flow (dashed lines) and circulation (arrows) within the LAA.

With the distal end portion 32 securely positioned within the LAA 22, the proximal end portion 30 of the implantable sprayer 26 can be anastomosed with an artery 60. As shown in FIG. 8, the proximal end portion 30 can be anastomosed with the right subclavian artery 66. Upon anastomosis with the right subclavian artery 66, blood can flow through the elongated tubular body 28 of the implantable sprayer 26 and be sprayed out of the at least one opening 42. Blood can then be continuously sprayed out of the at least one opening 42 to increase circulation throughout the LAA 22 and thereby prevent or mitigate blood stagnation (FIG. 9). By increasing blood circulation, thrombus formation within the LAA 22 can be prevented or mitigated.

Current methods for preventing thrombus formation in the LAA 22 include: (1) surgical ligation of the LAA; (2) implanting a LAA occluder (not shown) to prevent or mitigate blood flow into the LAA; and (3) placing a filter (not shown)

in the LAA ostium to prevent clots formed therein from re-entering the circulatory system. Advantageously, the method 10 of the present invention does not surgically obliterate the LAA 22 or occlude the LAA ostium. Rather, the present invention provides an alternative and continuous path of blood into the LAA 22 that increases blood circulation therein and prevents or mitigates thrombosis.

Figure 10:
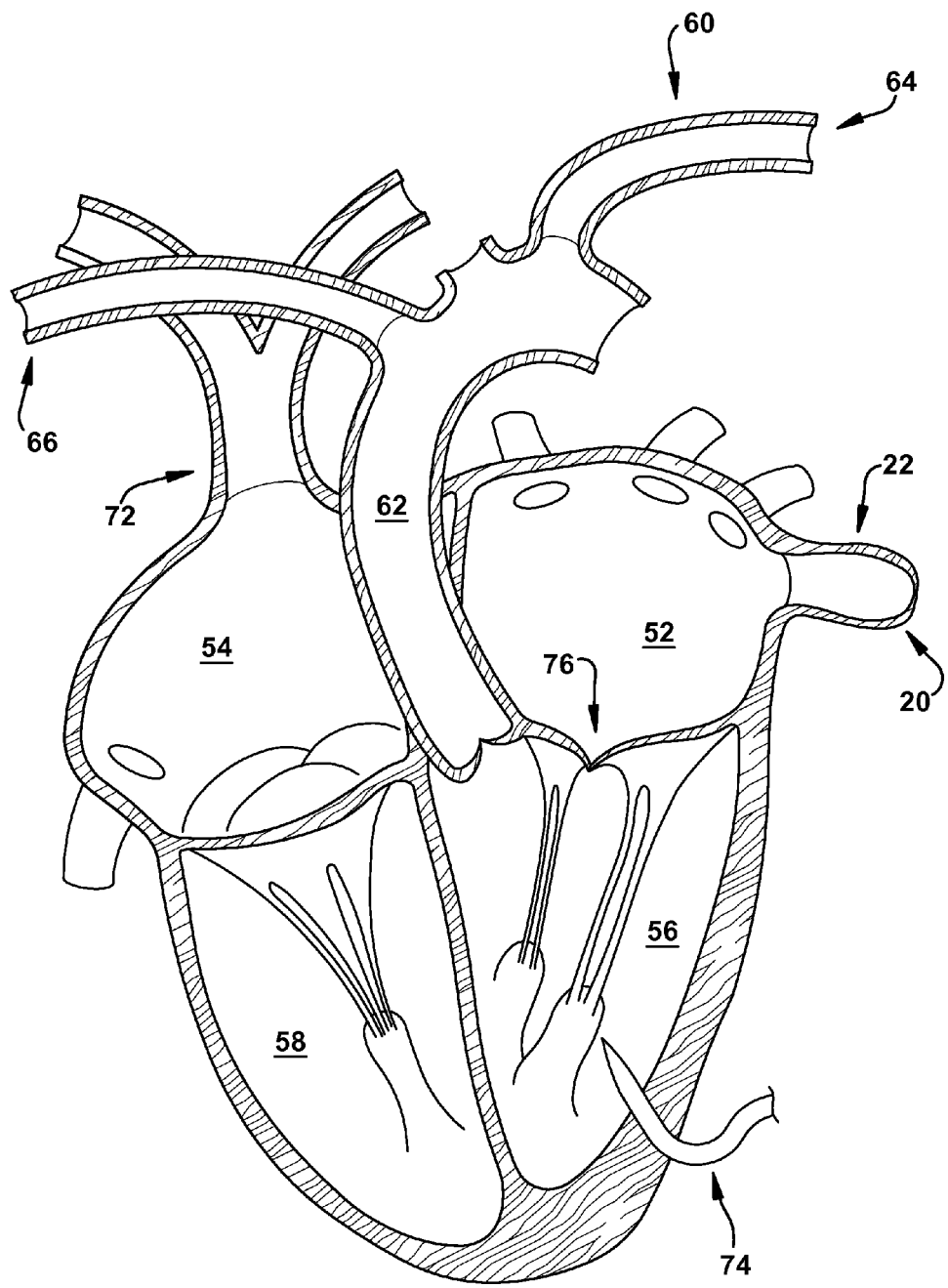
FIG. 10 is a cross-sectional view of a human heart showing a puncture tool being used to form an apical puncture in the left ventricle.
Figure 11:
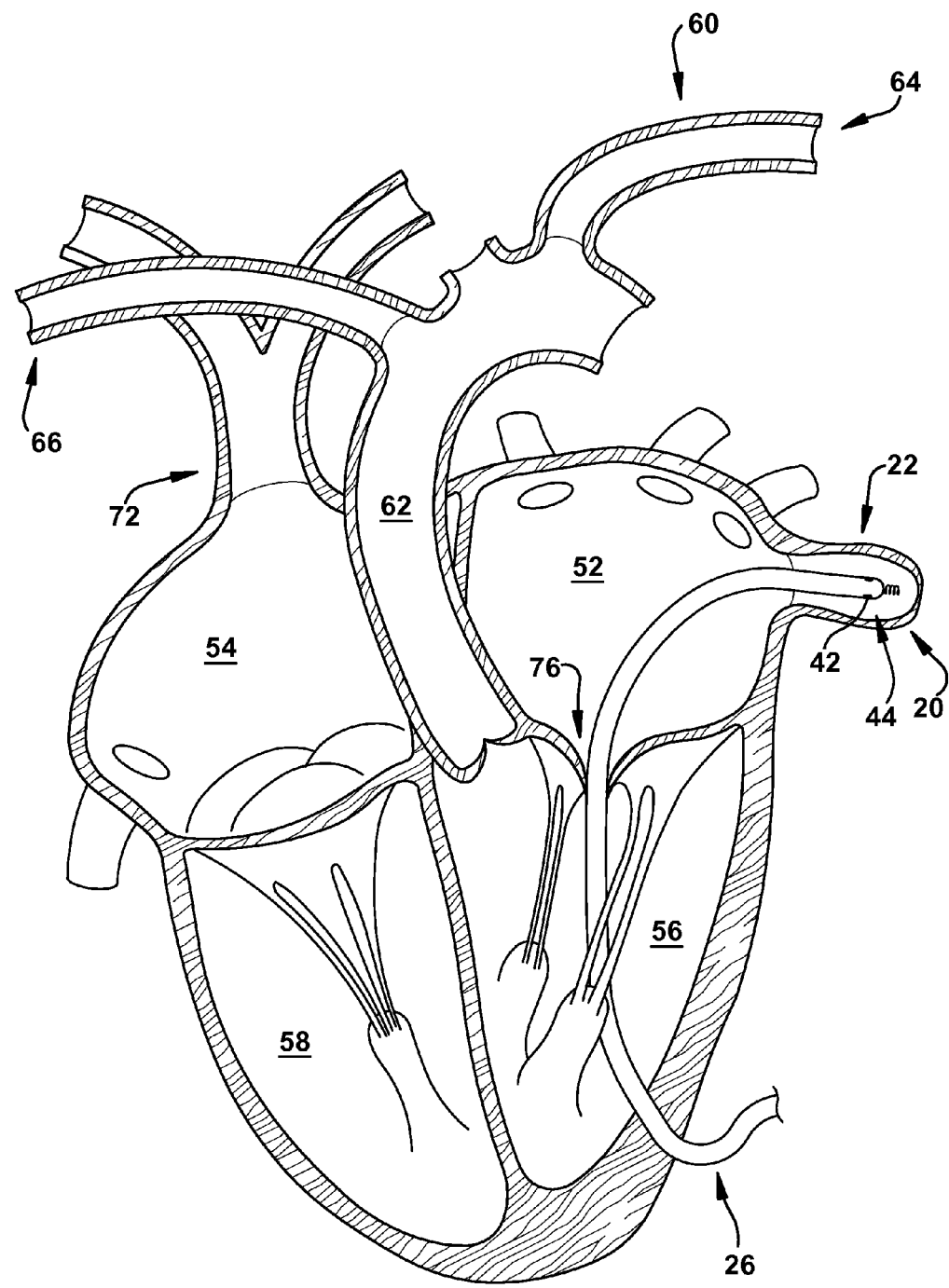
FIG. 11 is a cross-sectional view of the human heart in FIG. 10 showing the implantable sprayer (FIG. 2) being inserted through the mitral valve and advanced into the LAA.
Figure 12:
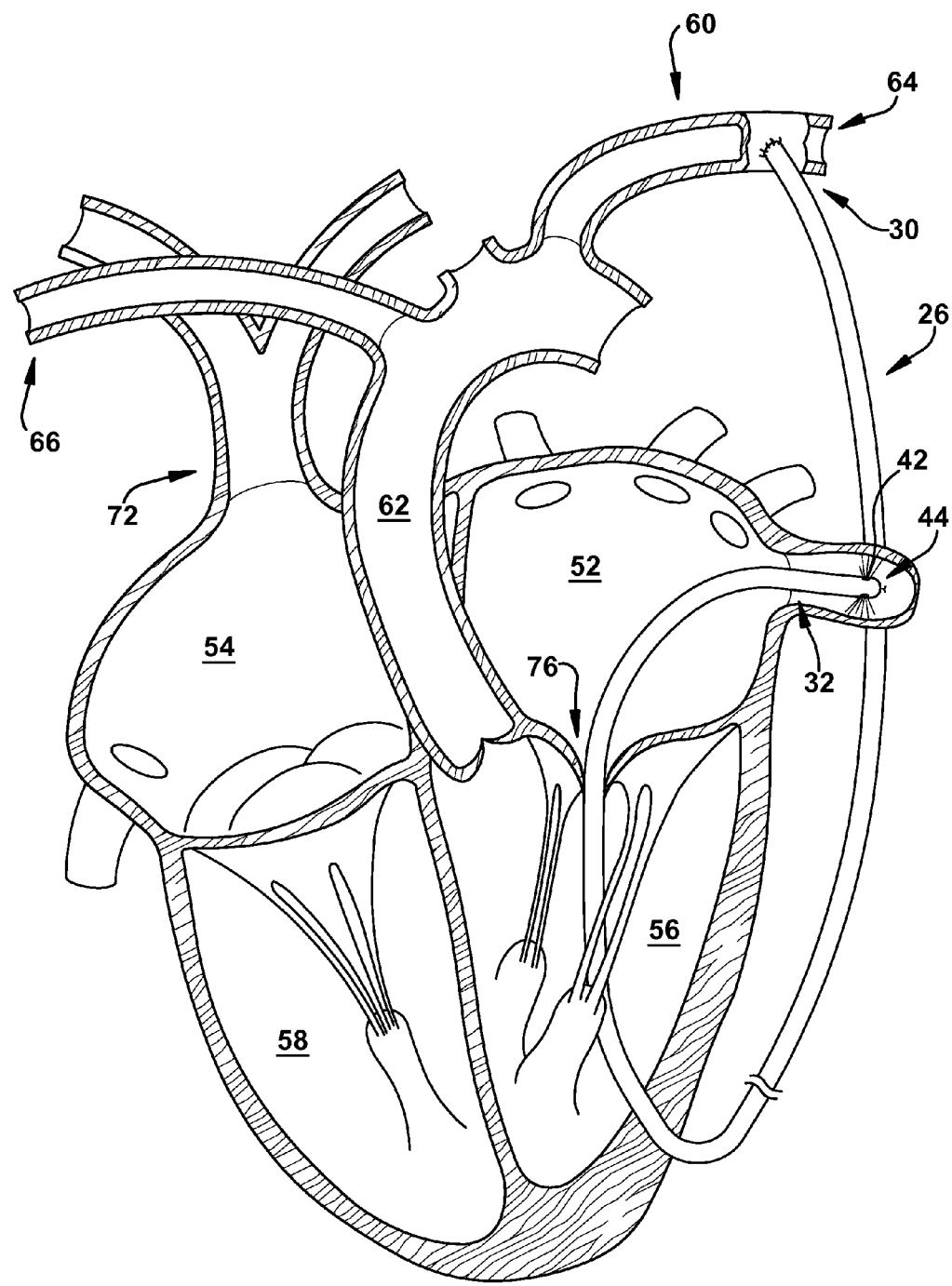
FIG. 12 is a cross-sectional view of the human heart in FIG. 11 showing the flow of blood (dashed lines) from the distal end portion of the implantable sprayer upon anastomosis of the proximal end portion with the left subclavian artery.

Another example of a method for increasing blood flow in the LAA 22 to prevent thrombosis is illustrated in FIGS. 10-12. The method illustrated in FIGS. 10-12 is a transapical approach that can be performed as an alternative to, or in conjunction with, the transseptal approach discussed above. The method can begin by selecting an appropriately-sized implantable sprayer 26 (as discussed above), and then determining the dimensions of the left ventricle 56, the left atrium 52, and the LAA 22 using one or a combination of known imaging techniques (e.g., MRI, fluoroscopy, echocardiography, CT, angiography, ultrasound, etc.). Next, a puncture tool 74 (FIG. 10) can be used to puncture a portion of the left ventricular apex. One skilled in the art will appreciate that the particular puncture tool 74 used to puncture the apex will depend upon the intended location of the puncture, the overall size of the puncture, the anatomy of the subject, the subject's age, any underlying co-morbidities, and/or any prior cardiac surgeries.

After forming the apical puncture, a flexible guidewire (not shown) can be inserted through the puncture and then advanced into the left atrium 52 to facilitate insertion of the implantable sprayer 26. Once the guidewire is appropriately-positioned, the implantable sprayer 26 can be loaded onto the guidewire along with a delivery sheath (not shown), if desired. As shown in FIG. 11, the distal end portion 32 of the implantable sprayer 26 can then be advanced through the apical puncture into the left ventricle 52, through the mitral valve 76, and into the LAA 22. With the distal end portion 32 properly positioned in the LAA 22, the anchoring mechanism 44 (e.g., the spiral-shaped member 46) can be deployed to securely anchor the distal end portion. For example, an axial force can be applied to the implantable sprayer 26 (e.g., by tactile means) so that the second sharpened end 50 of the spiral-shaped member 46 pierces a portion of the tissue comprising the LAA 22. Next, a sufficient amount of torque can be applied to the implantable sprayer 26 to cause the spiral-shaped member 46 to become securely embedded with the tissue of the LAA 22.

With the distal end portion 32 securely positioned within the LAA 22, the proximal end portion 30 of the implantable sprayer 26 can be anastomosed with an artery 60. As shown in FIG. 12, the proximal end portion 30 can be anastomosed with the left subclavian artery 64. Upon anastomosis with the left subclavian artery 64, blood can flow through the elongated tubular body 28 of the implantable sprayer 26 and be sprayed out of the at least one opening 42. Blood can then be continuously sprayed out of the at least one opening 42 to increase blood circulation throughout the LAA 22 to prevent or mitigate blood stagnation and thus prevent or mitigate thrombosis.

Figure 13:
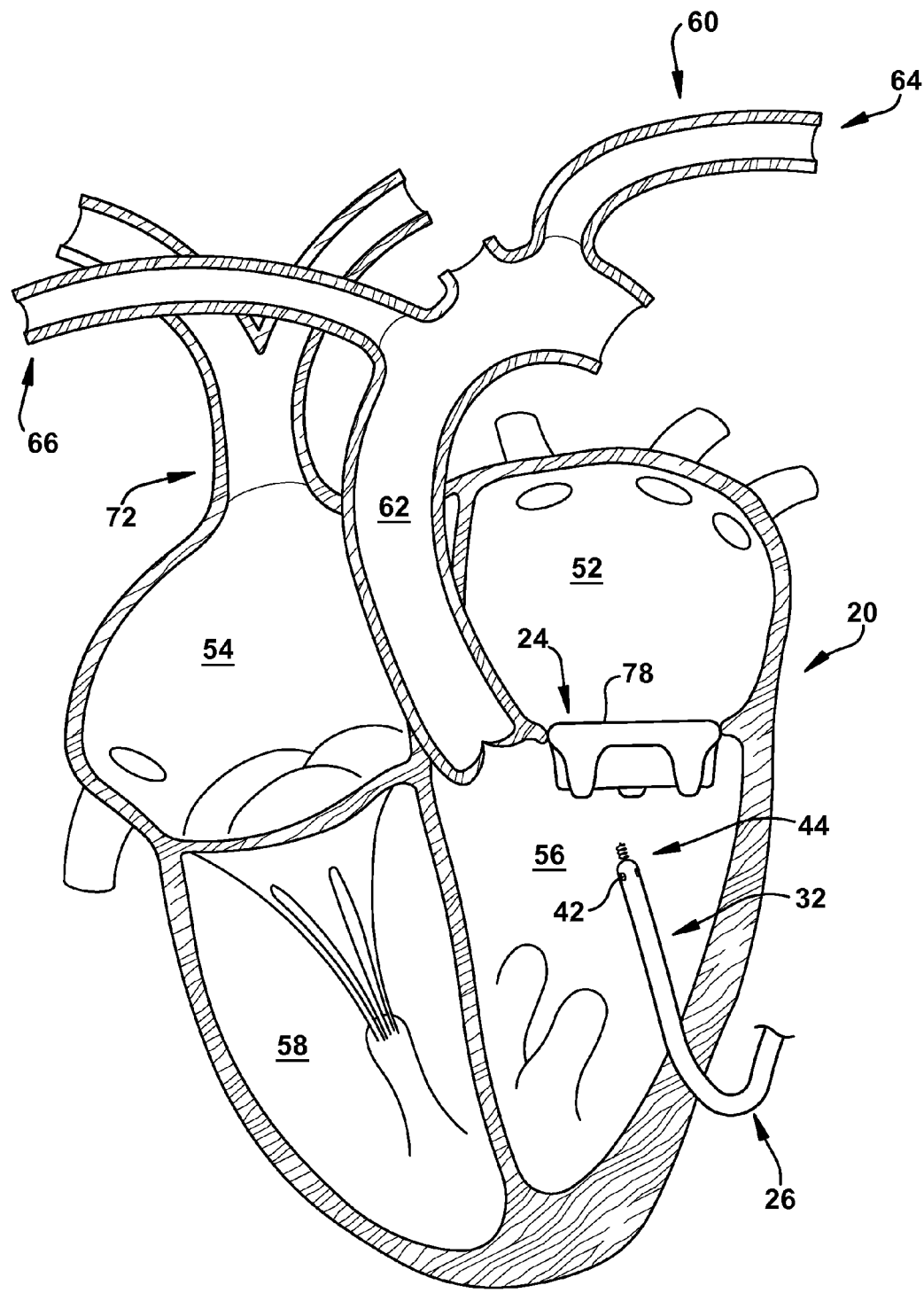
FIG. 13 is a cross-sectional view of a human heart showing the implantable sprayer (FIG. 2) being inserted through an apical puncture and advanced to an implanted prosthetic mitral valve.
Figure 14:
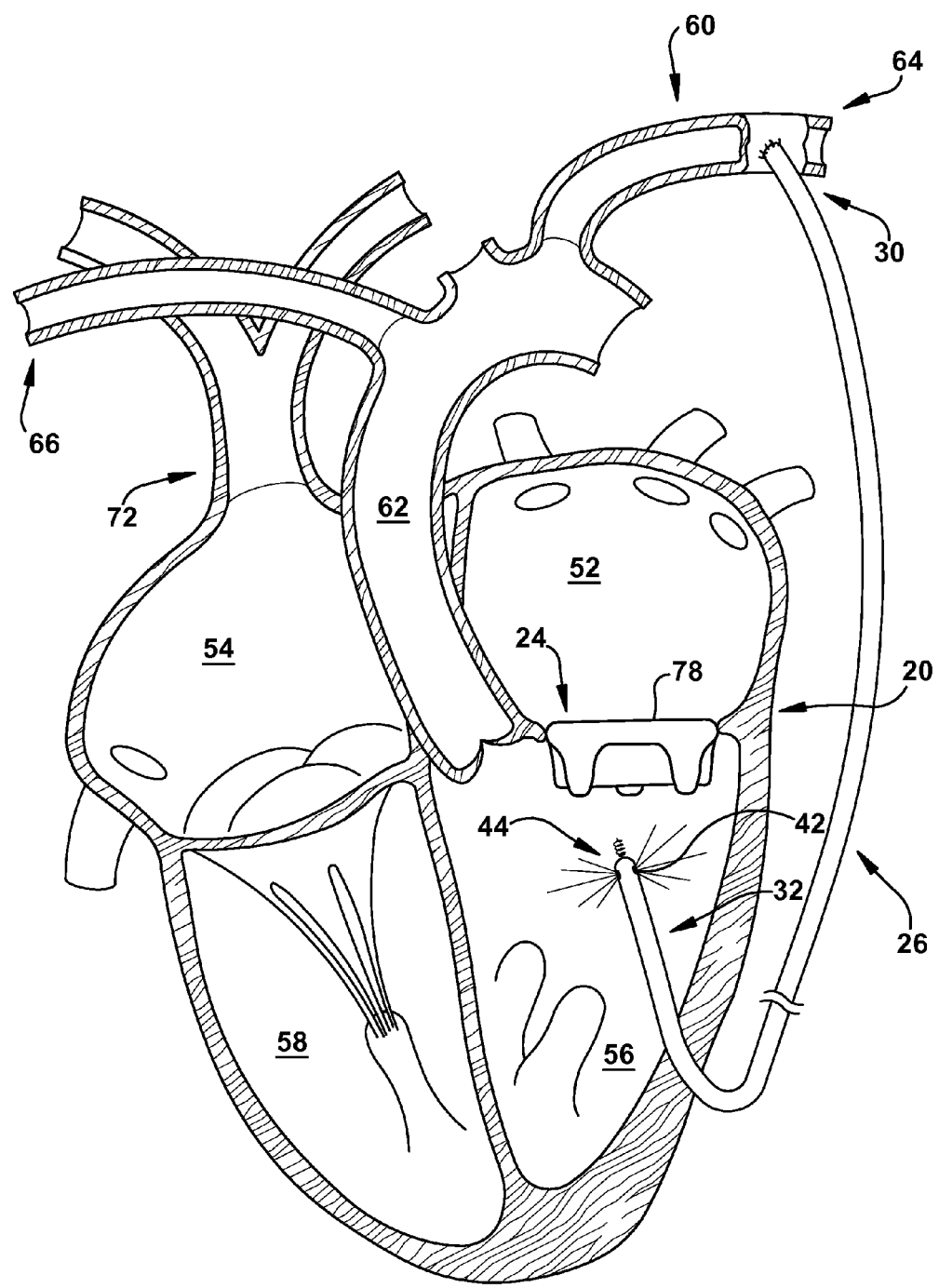
FIG. 14 is a cross-sectional view of the human heart in FIG. 13 showing the flow of blood (dashed lines) from the distal end portion of the implantable sprayer about an inferior aspect of the implanted prosthetic mitral valve upon anastomosis of the proximal end portion with the left subclavian artery.

Yet another example of the present invention can include a method for increasing blood flow about an implanted prosthetic cardiac valve 24 to prevent thrombosis (FIGS. 13-14). Prosthetic valve thrombosis can be defined by any thrombus, in the absence of infection, attached to or near an implanted valve 24 that occludes part of the blood flow or interferes with valvular function. Prosthetic valve thrombosis can be a dreaded complication of patients with mechanical heart valves, particularly those in the mitral position. Acute obstruction can be a life-threatening complication caused by the formation of fresh clot or fibrous tissue overgrowth, or both. As described in more detail below, the method illustrated in FIGS. 13-14 advantageously provides continuous blood circulation about an implanted prosthetic cardiac valve 24 to prevent or mitigate thrombus formation by reducing blood stasis about the valve.

Although FIGS. 13-14 illustrate a transapical approach for increasing blood flow about an implanted prosthetic mitral valve 78, it will be appreciated that other surgical approaches may additionally or alternatively be used. For example, a transseptal approach like the one illustrated in FIGS. 5-9 and described above may be used. As described above, the method can begin by selecting an appropriately-sized implantable sprayer 26. Prior to selecting the implantable sprayer 26, the dimensions of the left ventricle 56, the left atrium 52, and the LAA 22 can be determined using one or a combination of known imaging techniques (e.g., MRI, fluoroscopy, echocardiography, CT, angiography, ultrasound, etc.).

Next, a puncture tool 74 can be used to puncture a portion of the left ventricular apex (as discussed above). After forming an apical puncture, a flexible guidewire can be inserted through the puncture and then advanced into the left atrium 52 to facilitate insertion of the implantable sprayer 26. Once the guidewire is appropriately-positioned, the implantable sprayer 26 can be loaded onto the guidewire along with a delivery sheath, if desired.

As shown in FIG. 13, the distal end portion 32 of the implantable sprayer 26 can then be advanced through the apical puncture into the left ventricle 56, just inferior to the implanted prosthetic mitral valve 78. Once the distal end portion 32 is appropriately positioned in the left ventricle 56, the anchoring mechanism 44 (e.g., the spiral-shaped member 46) can be deployed to securely anchor the distal end portion. For example, an axial force can be applied to the implantable sprayer 26 (e.g., by tactile means) so that the second sharpened end 50 of the spiral-shaped member 46 pierces a portion of the left ventricular tissue. Next, a sufficient amount of torque can be applied to the implantable sprayer 26 to cause the spiral-shaped member 46 to become securely embedded with the left ventricular tissue. It will be appreciated that the distal end portion 32 can be anchored in other locations about the implanted prosthetic mitral valve 78, such as in the annular tissue surrounding the valve. Alternatively, the distal end portion 32 can be directly attached to a portion of the implanted prosthetic mitral valve 78 itself.

With the distal end portion 32 securely positioned about the implanted prosthetic mitral valve 78, the proximal end portion 30 of the implantable sprayer 26 can be anastomosed with an artery 60. As shown in FIG. 14, the proximal end portion 30 can be anastomosed with the left subclavian artery 64. Upon anastomosis with the left subclavian artery 64, blood can flow through the elongated tubular body 28 of the implantable sprayer 26 and be sprayed out of the at least one opening 42. Blood can then be continuously sprayed out of the at least one opening 42 to increase blood circulation about the inferior aspect of the implantable prosthetic mitral valve 78 and thereby wash the leaflets of the implanted prosthetic mitral valve. By increasing blood circulation about the implanted prosthetic mitral valve 78, thrombus formation can be prevented or mitigated.

Figure 15:
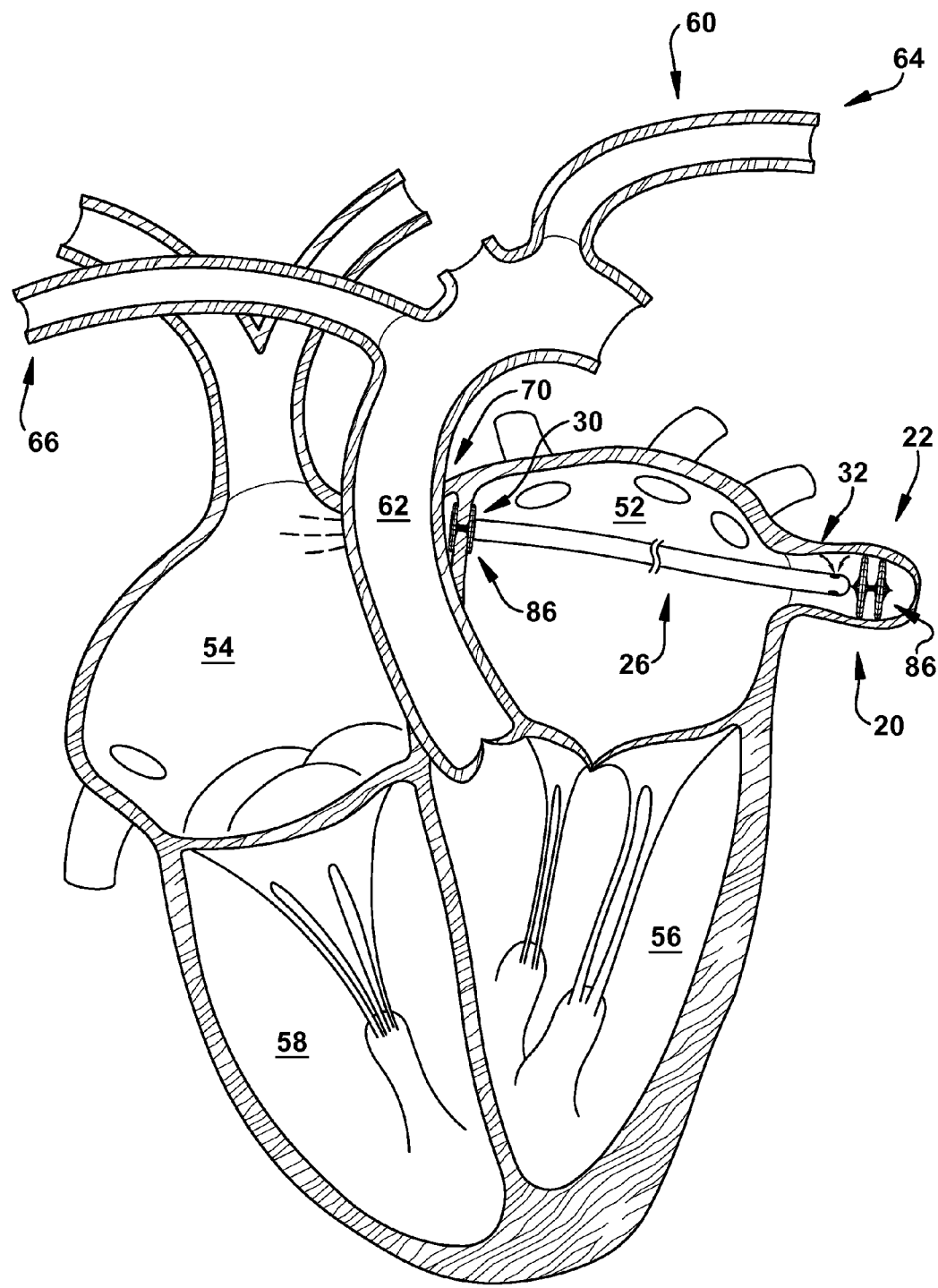
FIG. 15 is a cross-sectional view of a human heart showing the proximal end portion implantable sprayer of FIG. 2 anastomosed with the interatrial septum, and the distal end portion anchored in the LAA.

FIG. 15 illustrates another aspect of the present invention comprising a method for promoting blood circulation within a LAA 22. The method can be performed using a transseptal approach like the one illustrated in FIGS. 5-9 and described above. The method can begin by selecting an appropriately-sized implantable sprayer 26. For example, an implantable sprayer 26 similar or identical to the one shown in FIGS. 4C-D can be selected. As shown in FIG. 15, the proximal end portion 30 of the implantable sprayer 26 can also include a septal occluder 86. Prior to selecting the implantable sprayer 26, the dimensions of at least the left atrium 52 and the LAA 22 can be determined using one or a combination of known imaging techniques (e.g., MRI, fluoroscopy, echocardiography, CT, angiography, ultrasound, etc.).

Next, a puncture tool 74 can be used to puncture a portion of the left ventricular apex (as discussed above). After forming an apical puncture, a flexible guidewire can be inserted through the puncture and then advanced into the left atrium 52 to facilitate insertion of the implantable sprayer 26. Once the guidewire is appropriately-positioned, the implantable sprayer 26 can be loaded onto the guidewire along with a delivery sheath (if desired).

After forming the transseptal puncture, the implantable sprayer 26 can be loaded into the sheath and advanced through the venous vasculature. As described above, the distal end portion 32 of the implantable sprayer 26 can be advanced through the superior vena cava 72, into the right atrium 54, and through the transseptal puncture into the left atrium 52. The distal end portion 32 can then be further advanced to a desired position within the LAA 22.

Once the distal end portion 32 is appropriately positioned within the LAA 22, the anchoring mechanism 44 (e.g., the septal occluder 86) can be deployed to securely anchor the distal end portion. For example, the septal occluder 86 can self-expand upon introduction into the LAA 22 so that each of the discs 92 engages a respective interior surface portion of the LAA and thereby secures the distal end portion 32 of the implantable sprayer 26 therein. Alternatively, the septal occluder 86 can be manually-expanded using an expansion mechanism, such as via a screw-based mechanism (not shown) so that each of the discs 92 engages a respective interior surface portion of the LAA and thereby secures the distal end portion 32 of the implantable sprayer 26 therein.

With the distal end portion 32 securely positioned in the LAA 22, the proximal end portion 30 of the implantable sprayer 26 can be anastomosed with a portion of the interatrial septum 70 (e.g., at the transseptal puncture). As shown in FIG. 15, for example, the septal occluder 86 located at the proximal end portion 30 can be appropriately positioned and anchored across the interatrial septum 70 to secure the proximal end portion thereto. Upon anastomosis of the proximal end portion 30 with the interatrial septum 70, blood can be withdrawn (indicated by arrows) through the at least one opening 42 of the distal end portion 32 into the right atrium 54 (indicated by dashed lines) as a result of the pressure difference between the left atrium 52 and the right atrium (i.e., decreased right atrial pressure as compared to the left atrial pressure). Consequently, blood in the LAA 22 can be continuously withdrawn through the implantable sprayer 22 and thereby prevent or mitigate blood stasis in the LAA.

It will be appreciated that it may desirable to anastomose the proximal end portion 30 of the implantable sprayer 26 with a vein to increase blood flow in or about a cardiac structure 20. For example, the distal end portion 32 of the implantable sprayer 26 can be securely positioned in or about a cardiac structure 20 (as described above), followed by anastomosis of the proximal end portion 30 with a vein. If it has not been done so already, the implantable sprayer 26 can then be placed in-line with a cardiac pump (not shown) to pump blood from the vein through the implantable sprayer. The cardiac pump can include a sensor (not shown) that monitors and/or modulates the rate of blood flow through the implantable sprayer 26.

It will also be appreciated that the present invention can be employed to promote blood circulation and mitigate or prevent thrombosis in bodily locations other than those described above and shown in FIGS. 5-14. For example, the implantable sprayer 26 can be used to prevent or divert blood clots from the patent foramen ovale (not shown), when present. Additionally, the implantable sprayer 26 can be used to treat peripheral artery or vein disease by preventing or mitigating blood stasis. Further, one or more implantable sprayers 26 can be used to treat aneurysms and/or decreased blood flow in the left ventricle 56.

From the above description of the invention, those skilled in the art will perceive improvements, changes, and modifications. For example, it will be appreciated that more than one implantable sprayer 26 can be used to increase blood flow in or about the same or different cardiac structure(s) 20. Such improvements, changes, and modifications are within the skill of the art and are intended to be covered by the appended claims.

Having described the invention, the following is claimed:

1. A method for increasing blood flow in or about a cardiac structure to prevent thrombosis, the method comprising the steps of:
    providing an implantable sprayer, the implantable sprayer comprising an elongated tubular body having proximal and distal end portions, the distal end portion including at least one opening and an anchoring mechanism;
    deploying the anchoring mechanism so that the distal end portion of the implantable sprayer is secured in or about the cardiac structure; and
    anastomosing the proximal end portion with an artery so that blood flows through the elongated tubular body of the implantable sprayer and is sprayed out of the at least one opening to continuously circulate blood in or about the cardiac structure.

2. The method of claim 1, wherein said step of deploying the anchoring mechanism further comprises inserting the distal end portion of the implantable sprayer into a cardiac chamber that includes the cardiac structure.

3. The method of claim 2, wherein said step of inserting the distal end portion of the implantable sprayer into a cardiac chamber further comprises the step of forming a trans-septal puncture between a right atrium and a left atrium.

4. The method of claim 1, wherein said step of deploying the anchoring mechanism further comprises the step of securing the distal end portion in a left atrial appendage.

5. The method of claim 1, wherein said step of anastomosing the proximal end portion of the implantable sprayer with an artery further comprises the step of anastomosing the proximal end portion with a subclavian artery.

6. A method for increasing blood flow in a left atrial appendage to prevent thrombosis, the method comprising the steps of:
    providing an implantable sprayer, the implantable sprayer comprising an elongated tubular body having proximal and distal end portions, the distal end portion including at least one opening and an anchoring mechanism;
    inserting the distal end portion of the implantable sprayer into a left atrium that includes the left atrial appendage;
    deploying the anchoring mechanism so that the distal end portion of the implantable sprayer is secured in the left atrial appendage; and
    anastomosing the proximal end portion with a subclavian artery so that blood flows through the elongated tubular body of the implantable sprayer and is sprayed out of the at least one opening to continuously circulate blood in the left atrial appendage.

7. The method of claim 6, wherein said step of inserting the distal end portion of the implantable sprayer into a left atrium further comprises the steps of:
- puncturing a septum between a right atrium and the left atrium;
- inserting the distal end portion of the implantable sprayer into a subclavian vein; and
- advancing the distal end portion of the implantable sprayer into a superior vena cava into the left atrium via the septal puncture.

8. A method for promoting circulation within a left atrial appendage, said method comprising the steps of:
- providing an implantable sprayer, the implantable sprayer comprising an elongated tubular body having proximal and distal end portions, the distal end portion including at least one opening and an anchoring mechanism;
- inserting the distal end portion of the implantable sprayer into a left atrium that includes the left atrial appendage;
- deploying the anchoring mechanism so that the distal end portion of the implantable sprayer is secured in the left atrial appendage; and
- anastomosing the proximal end portion with a portion of an interatrial septum so that blood is withdrawn from the left atrial appendage through the at least one opening and into a right atrium to prevent or mitigate blood stasis in the left atrial appendage.

* * * * *